(12) United States Patent
Brandl et al.

(10) Patent No.: US 9,937,286 B2
(45) Date of Patent: Apr. 10, 2018

(54) MEDICAL FUNCTIONAL DEVICE, PROCESS FLUID, AND MEDICAL TREATMENT APPARATUS

(75) Inventors: Matthias Brandl, Bad Koenigshofen (DE); Michael Herrenbauer, Neu-Anspach (DE); Wolfgang Wehmeyer, Tuebingen (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 407 days.

(21) Appl. No.: 13/805,145

(22) PCT Filed: Jun. 27, 2011

(86) PCT No.: PCT/EP2011/003152
§ 371 (c)(1),
(2), (4) Date: Jan. 16, 2013

(87) PCT Pub. No.: WO2012/000637
PCT Pub. Date: Jan. 5, 2012

(65) Prior Publication Data
US 2013/0112629 A1    May 9, 2013

(30) Foreign Application Priority Data
Jun. 29, 2010   (DE) .................. 10 2010 025 516

(51) Int. Cl.
*A61M 1/36* (2006.01)
*A61M 1/16* (2006.01)

(52) U.S. Cl.
CPC .......... *A61M 1/3643* (2013.01); *A61M 1/168* (2013.01); *A61M 1/1682* (2014.02);
(Continued)

(58) Field of Classification Search
CPC .. A61M 1/3621; A61M 1/1682; A61M 1/168; A61M 1/16; A61M 1/14;
(Continued)

(56) References Cited
U.S. PATENT DOCUMENTS 3,946,731 A * 3/1976 Lichtenstein .................. 604/66
4,209,392 A * 6/1980 Wallace ........................ 210/646
(Continued)

FOREIGN PATENT DOCUMENTS

DE    38 75 127 T2    2/1993
DE    197 04 564 A1   8/1998
(Continued)

OTHER PUBLICATIONS

International Search Report from PCT/EP2011/003152 dated Oct. 18, 2011.
(Continued)

*Primary Examiner* — David C Mellon
*Assistant Examiner* — Liam Royce
(74) *Attorney, Agent, or Firm* — Fish & Richardson P.C.

(57) ABSTRACT

A medical functional device, provided and designed for single use in a method for extracorporeally treating the blood of a patient, includes at least one process fluid circuit or sections thereof, each provided for receiving a process fluid, at least one first filter device arranged within the process fluid circuit or a section thereof and at least one second filter device arranged within the process fluid circuit or a section thereof. The present invention further relates to a process fluid and a medical treatment apparatus.

16 Claims, 2 Drawing Sheets

(52) U.S. Cl.
CPC .......... *A61M 1/365* (2014.02); *A61M 1/3644* (2014.02); *A61M 1/3649* (2014.02); *A61M 2205/126* (2013.01)

(58) Field of Classification Search
CPC .............. A61M 1/3649; A61M 1/3644; A61M 1/3643; A61M 1/36; A61M 1/365; A61M 1/0066–1/0076; A61M 1/101; A61M 1/1601; A61M 2205/126; B01D 69/08; B01D 61/24–61/30
USPC ............... 210/650, 649, 634, 646, 645, 644; 604/5.04, 5.01, 6.09, 6.1, 6.11, 66, 65, 48
See application file for complete search history.

(56) References Cited

U.S. PATENT DOCUMENTS

| | | | |
|---|---|---|---|
| 4,211,597 A | 7/1980 | Lipps et al. | |
| 4,661,246 A | 4/1987 | Ash | |
| 5,423,738 A | 6/1995 | Robinson et al. | |
| 5,893,382 A | 4/1999 | Puppini | |
| 7,507,217 B2 | 3/2009 | Ferrari | |
| 2001/0032818 A1 | 10/2001 | Nikaido et al. | |
| 2002/0104800 A1* | 8/2002 | Collins et al. | 210/646 |
| 2004/0019312 A1 | 1/2004 | Childers et al. | |
| 2005/0040110 A1 | 2/2005 | Felding | |
| 2005/0131332 A1* | 6/2005 | Kelly | A61M 1/1696 604/4.01 |
| 2005/0230292 A1 | 10/2005 | Beden et al. | |
| 2007/0208292 A1 | 9/2007 | Ferrari | |
| 2009/0101550 A1 | 4/2009 | Muller et al. | |

FOREIGN PATENT DOCUMENTS

| | | |
|---|---|---|
| DE | 100 11 208 C1 | 9/2001 |
| DE | 696 23 563 T2 | 5/2003 |
| DE | 10 2004 011461 A1 | 9/2005 |
| DE | 10 2005 022545 B4 | 11/2006 |
| DE | 10 2006 012087 A1 | 9/2007 |
| EP | 0277839 A2 | 8/1988 |
| EP | 00992254 | 4/2000 |
| JP | S63154181 A | 6/1988 |
| JP | H06-269496 | 9/1994 |
| JP | 2000107284 | 4/2000 |
| JP | 2004524083 | 8/2004 |
| JP | 2005528168 | 9/2005 |
| JP | 2008055185 A | 3/2008 |
| WO | 02/062454 A1 | 8/2002 |
| WO | 03/043680 A1 | 5/2003 |
| WO | 2005044339 | 5/2005 |
| WO | 2009055639 A2 | 4/2009 |

OTHER PUBLICATIONS

Japanese Search Report by Registered Searching Organization in Japanese Application No. 2013-517072, dated Apr. 28, 2015, 43 pages (with English translation).

* cited by examiner

MEDICAL FUNCTIONAL DEVICE, PROCESS FLUID, AND MEDICAL TREATMENT APPARATUS

CROSS REFERENCE TO RELATED APPLICATIONS

The present application is the national stage entry of International Patent Application No. PCT/EP2011/003152, filed on Jun. 27, 2011, which claims priority to Application No. DE 10 2010 025 516.5, filed in the Federal Republic of Germany on Jun. 29, 2010.

FIELD OF INVENTION

The present invention relates to a medical functional device, a method, a process fluid and a medical treatment apparatus.

BACKGROUND INFORMATION

It is known from practice to prime, rinse or fill blood conducting devices, respectively, for extracorporeal blood treatment, such as lines, filters, cassette units of dialyzing machines, and the like, prior to their use in a blood treatment process using a process fluid not being blood.

SUMMARY

One object of the present invention is to propose another medical functional device enabling priming or rinsing and/or filling an extracorporeal blood circuit by using a process fluid.

All or some of the advantages achievable by means of the medical functional device according to the present invention can likewise undiminishedly be obtained by means of the process fluid according to the present invention and/or the medical treatment apparatus according to the present invention.

According to the present invention, there is proposed an internal or external medical or medical-technical functional device, comprising at least one process fluid circuit or sections thereof each being provided for receiving a process fluid. The medical functional device further comprises at least one first filter device and at least one second filter device each being arranged within the process fluid circuit or a section thereof.

The medical functional device is provided and designed or embodied, respectively, for single or one-time, respectively, use in a method for extracorporeally treating the blood of a patient. It can be designed or embodied, provided and/or marketed as a disposable, a single use article, or the like.

The method according to the present invention relates to operating a medical functional device according to the present invention and comprises completely or partially opening a second valve device and/or an occluding pumping device for cleaning the first filter device.

The process fluid according to the present invention is treated, produced, filtrated and/or sterilized by using a medical functional device according to the present invention.

The medical treatment apparatus according to the present invention is provided and configured for receiving and/or controlling at least one medical functional device according to the present invention and/or for performing the method according to the present invention.

Exemplary embodiments according to the present invention may comprise some or all of the following features in an arbitrary combination.

The medical treatment apparatus is provided for its use in extracorporeal blood treatment methods.

In some exemplary embodiments according to the present invention, the medical treatment apparatus is a blood cleaning apparatus such as a hemodialyzing apparatus, a hemofiltration apparatus, a hemodiafiltration apparatus. It can be an apparatus for performing a liver support therapy, an apparatus for performing an immunoadsorption, or the like.

The term "method for extracorporeally treating the blood of a patient," in the following also referred to as an "extracorporeal blood treatment method," relates to a method for extracorporeally treating blood.

Prior to performing the extracorporeal blood treatment method, by which the extracorporeal treatment of the blood shall be carried out, a number or a plurality of single processes or process steps may be required such as rinsing or priming and/or filling the extracorporeal blood circuit by using a process fluid.

A process fluid used in a process of the extracorporeal blood treatment method can be intended to fulfill several functions such as, for example, serving as a rinsing and/or filling fluid, as a displacement fluid or as a sterilization fluid, and the like.

The process fluid can be a fluid in general, preferably a liquid or a combination or mixture of different fluids in general or liquids.

The process fluid can be supplied to or introduced, respectively, and/or conveyed within the process fluid circuit by means of or under the effect of a conveying device.

Such a—first—conveying device can be provided in the process fluid circuit as a part of the medical functional device or as an external conveying device as regards the medical functional device. The conveying device does not have to be part of the functional device.

In certain exemplary embodiments, the conveying device is selected from membrane pumps, peristaltic pumps and/or impeller pumps.

In certain exemplary embodiments of the present invention, the conveying device is arranged in the process fluid circuit in order to convey process fluid from a process fluid source into the process fluid circuit.

In certain exemplary embodiments, the medical functional device according to the present invention comprises at least one conveying device which is arranged in or on the medical functional device, preferably as a part thereof, in the process fluid circuit in order to convey the process fluid within the process fluid circuit or within a section thereof.

This—second—conveying device can be arranged in or on the medical functional device, in preferred exemplary embodiments as a part thereof, in the process fluid circuit. Being a part of the medical functional device, in particular of a disposable functional device, the second conveying device can be designed and provided for single use.

In certain exemplary embodiments according to the present invention of the medical functional device, the extracorporeal blood circuit or sections thereof can or will be coupled or connected with the medical functional device or form a part of the medical functional device.

In some exemplary embodiments of the medical functional device according to the present invention, parts or portions, respectively, of the extracorporeal blood circuit such as, for example, channels, tube sections, lines or line sections, can be designed integrally with the medical functional device or can be connected with the medical functional device in any other way.

In addition to lines, such as, for example, an arterial and a venous patient line, the extracorporeal blood circuit can comprise tubings, tubing systems, channels, valves, treatment devices, respectively, such as, for example, filter and/or dialyzing devices, conveying devices, and the like.

The term "process fluid circuit" as used herein denotes a fluid system or a fluid arrangement, suited and provided for receiving and being flown through by process fluids. The process fluids can be used for the purpose of a process like rinsing, priming, substituting, reducing the concentration of toxic substances, and the like.

The process fluid circuit can completely or in sections be part of the medical functional device according to the present invention.

In some exemplary embodiments of the medical functional device according to the present invention, sections of the process fluid circuit can be designed integrally with the medical functional device or can be integrated in the medical functional device, respectively.

In certain exemplary embodiments, process fluid conducting sections of the process fluid circuit such as lines, e.g., in form of tubings, are part of the medical functional device.

The process fluid circuit can comprise lines, tubings, tubing systems, channels, valves, throttles, filter devices, sensors, chambers, indentations, devices or spaces or areas for storing or retaining process fluids as well as controlling devices for controlling or regulating a fluid flow of the process fluids, conveying devices for conveying the process fluids, and the like or may consist of arbitrary combinations thereof.

The process fluid circuit can be a closed circuit or closed loop, respectively. The process fluid circuit can, however, also be part of a (superior) fluid circuit. The process fluid circuit can be an open circuit.

In certain exemplary embodiments of the present invention, for the purpose of use, the medical functional device is connectable or connected with at least one process fluid source.

Optionally in combination with a reception device for used process fluid, the process fluid source can be part of a process fluid supply unit.

The process fluid source can be an apparatus for online preparation, i.e., for a preparation carried out during the extracorporeal blood treatment method, of process fluid. However, the process fluid source may also be a source providing charges or portions of process fluids, for example, a bag filled with process fluid or pre-stages thereof, and the like.

The present invention also encompasses combinations of different process fluid sources for providing one or more different process fluids.

In certain exemplary embodiments according to the present invention, the process fluid source is arranged in a first line section of the process fluid circuit in flow direction of the process fluid upstream the first filter device. In those exemplary embodiments, it is envisaged to supply the process fluid from the process fluid source to the first filter device of the process fluid circuit.

In order to interrupt or prevent, respectively, (or in order to only reduce) and/or release a process fluid flow in and/or within the process fluid circuit, in some exemplary embodiments according to the present invention, appropriate flow reducing or preventing devices such as valve devices, through-flow blocking devices such as shut-off valves, clamps, and the like can be provided. Additionally or alternatively, flow permitting or flow releasing devices, respectively, or further conveying devices in addition to the afore-mentioned conveying devices can be provided.

In certain exemplary embodiments according to the present invention of the medical functional device, at least one valve device is arranged in the process fluid circuit. In certain exemplary embodiments, the valve device is arranged downstream the second filter device. In those exemplary embodiments, a process fluid flow from the second filter device within the process fluid circuit back to the process fluid source or in the direction thereof can be prevented.

In certain exemplary embodiments of the present invention, the valve device is designed or embodied, respectively, and/or provided for, preferably at least temporarily and in an intended manner, preventing a through-flow of the process fluid from the second filter device through the further process fluid circuit.

In those exemplary embodiments, the valve device is provided and designed to partially or completely block a line section of the process fluid circuit downstream the second filter device.

Optionally, for example, in exemplary embodiments comprising a cascade filtration, at least one further valve device can be provided besides the afore-mentioned, i.e.,—in a case of at least two valve devices—first, valve device in the process fluid circuit.

In certain exemplary embodiments according to the present invention of the medical functional device, the further, i.e., in this case second, valve device is arranged downstream the first filter device. In those exemplary embodiments, a reflux or backflow, respectively, of the process fluid from a drain line into the process fluid circuit to the first filter device and/or in reverse direction can be prevented.

In certain exemplary embodiments—alternatively or additionally to the valve device downstream the second filter device and/or to the valve device downstream the first filter device—a conveying device, in particular a pump intended for proportional regulation, is arranged downstream the second filter device in the process fluid circuit.

In certain exemplary embodiments, a second valve device and/or an occluding pump is provided downstream the first filter device. It can, e.g., be provided in a drain line. By means of this arrangement, cleaning the first filter device can be carried out and operated by opening the said.

The medical functional device can be functionally coupleable to a medical blood treatment apparatus or may be present in a state coupled thereto.

A functional coupling of the medical functional device to the medical treatment apparatus can serve for achieving a control of the medical functional device in any way, for example, mechanically, pneumatically, electrically, electronically and/or for the purpose of data transmission.

In some exemplary embodiments according to the present invention, the medical treatment apparatus comprises one or more control devices such as internal or external control devices, and/or actuators that are provided and configured for controlling or regulating at least one medical functional device according to the present invention.

In certain exemplary embodiments of the present invention, the medical functional device is provided and/or configured for being controlled upon its coupling or connecting with a medical treatment apparatus such that introducing or supplying, respectively, process fluid into the process fluid circuit and/or the extracorporeal blood circuit can be prompted by correspondingly switching at least the valve device downstream the second filter device in the process fluid circuit and/or by actuating at least one of the conveying devices in the process fluid circuit.

In certain exemplary embodiments of the present invention, the medical functional device is provided and/or configured for being controlled upon its coupling or connecting with a medical treatment apparatus such that introducing or supplying, respectively, process fluid into the process fluid circuit and/or the extracorporeal blood circuit can be prompted by correspondingly switching at least the first valve device downstream the second filter device and the second valve device upstream the first filter device in the process fluid circuit and/or by actuating at least one of the conveying devices in the process fluid circuit.

Independently from the design of other valve devices in the corresponding exemplary embodiments, each of the valve devices can be provided and arranged in order to interrupt or release a process fluid flow along or within the process fluid circuit by correspondingly switching/controlling by means of the control device of the medical blood treatment apparatus or manually.

Independently from the design of other valve devices in the corresponding exemplary embodiments, each of the valve devices can be provided and arranged in order to allow a process fluid flow through the second filter device into the extracorporeal blood circuit by correspondingly switching/controlling by means of the control device of the medical blood treatment apparatus or manually.

In certain operating states of the medical functional device, a passover or transfer of the process fluid out of the process fluid circuit into the extracorporeal blood circuit is envisaged or intended.

The transfer of the process fluid out of the process fluid circuit into the extracorporeal blood circuit can occur in or within, respectively, or by means of a filter device, in particular the second filter device.

The term "filter device" as used herein generally refers to a device which is—completely or in sections—designed for filtrating, i.e., cleaning, optionally sterilizing, and the like, the process fluid. The filter devices provided in the medical functional device according to the present invention are embodied as disposables.

The first filter device or the second filter device can be a sterile filter. The use of a sterile filter can advantageously contribute to increasing the safety of the process fluid sterility.

Like the second filter device, the first filter device can comprise (one or more) hollow fiber capillary membranes and/or be a hollow fiber filter module. The first filter device can be completely or in sections integrated in or integrally connected with, respectively, the medical functional device. The same also applies for the second filter device.

In certain exemplary embodiments of the medical functional device according to the present invention, the second filter device is a blood filter device of the extracorporeal blood circuit. Appropriate blood filter devices include filter devices for performing a hemodialysis, a hemofiltration or a hemodiafiltration.

In certain exemplary embodiments of the present invention, the medical functional device according to the present invention is used for rinsing and/or filling the extracorporeal blood circuit. In those exemplary embodiments, the process fluid can preferably be a rinsing liquid such as a dialyzing liquid, a substitution liquid, a saline solution, and the like.

In certain exemplary embodiments of the present invention, the medical functional device according to the present invention is used and provided for the blood return in connection with an extracorporeal blood treatment and/or for bolus addition (e.g., of drug solutions, and the like) during an extracorporeal blood treatment.

In certain exemplary embodiments of the present invention, the medical functional device is provided and/or configured for being controlled such that it is switchable between a rinsing and/or filling process and a blood treatment process—for example, by means of a corresponding control of a machine.

This can be achieved by switching and/or controlling the valves and/or the (one or more) conveying devices.

In certain exemplary embodiments of the present invention, the rinsing and/or filling process serves for perfusing the blood conducting lines of the extracorporeal blood circuit with rinsing liquid in order, for example, to press air out of the lines, to effuse particles and/or to improve the wettability of the line interior with blood. Hereby, the extracorporeal blood circuit can be cleaned by rinsing the line interior and/or the interior of blood conducting device of the extracorporeal blood circuit prior to it being filled with blood.

In other exemplary embodiments according to the present invention, the process fluid can be a drug solution and/or an infusion solution such as, for example, a drug and/or infusion solution for bolus addition or for continuous addition, and the like. Examples thereof include a bolus addition into the blood circuit for the purpose of volume expansion or a bolus addition for changing the composition of the blood plasma, and the like, without being limited thereto.

In other exemplary embodiments according to the present invention, the process fluid can be used for blood return. By means of the transfer of the process fluid across a membrane of the second filter device into a blood conducting section thereof, the blood can be returned from the extracorporeal blood circuit to the patient after termination of the blood treatment. The transferred process fluid hereby displaces the blood out of the blood conducting section into a venous and/or an arterial line section of the extracorporeal blood circuit.

In those exemplary embodiments, optical detectors can be provided at the arterial and/or the venous patient line, detecting a phase interface or boundary, respectively, between blood and process fluid and prompting or inducing, respectively, a stop of the return process. Further features and/or embodiments of the blood return may, of course, also be envisaged without limiting the present invention to the exemplary embodiments mentioned-above.

The medical functional device according to the present invention and the basic principle thereof can advantageously be used in a push/pull hemodiafiltration as well as in other push-pull methods. Herewith, it can, for example, be possible to provide a solution for the volume exchange of the said methods.

The passover or transfer of the process fluid out of the process fluid circuit into the extracorporeal circuit can be achieved by generating a pressure difference.

In certain exemplary embodiments of the present invention, the conveying device corresponding to the conveying device above referred to as second conveying device being a part of the functional device is arranged in the process fluid circuit between the first and the second filter devices.

In addition to the first conveying device primarily serving for conveying the process fluid from the process fluid source, the second conveying device can contribute to transferring of the process fluid out of the process fluid circuit into the extracorporeal circuit.

In certain exemplary embodiments of the present invention, the second conveying device is provided and configured for being operated by means of an actuator of the medical treatment apparatus.

Thereby, in some exemplary embodiments according to the present invention, the actuator for actuating or operating, respectively, the second conveying device is not designed or embodied as a disposable, but is rather designed or embodied reusably, for example, as being a part of the medical functional device. Merely the device which, in the medical functional device, is in material contact with the process fluid and thus effects the pressure gradient, in some exemplary embodiments is embodied as a disposable.

In certain exemplary embodiments of the medical functional device according to the present invention, the second conveying device is selected from membrane pumps, peristaltic pumps and/or impeller pumps.

According to the present invention, the medical functional device is designed as a single-use article, i.e., a disposable. In certain exemplary embodiments according to the present invention, it is designed in form of a blood cassette, for example, in form of a single use blood cassette.

In some exemplary embodiments, the medical functional device according to the present invention, e.g., in form of a blood cassette, can comprise a plurality of functions which are completely or partly intended for single use. Such functions can include, e.g., valve devices, pumps, air separators, balancing systems, dialysate heating, etc.

Exemplary embodiments of the present invention can comprise one or more of the following advantages.

The present invention advantageously provides a simplified system for supplying or introducing, respectively, process fluid into an extracorporeal blood circuit in connection with an extracorporeal blood treatment method.

The two-stage filtration of the process fluid intended in the medical functional device of the present invention can reduce the contamination risk of the process fluid or of blood conducting sections of an extracorporeal blood circuit in case of filter failure and can thus advantageously contribute to increasing the system's safety. According to the present invention, the two-stageability can—nearly without any additional effort—be achieved by reversing the filtrate flow in the second filter device; as the outlet of the second filter device on the process fluid side may be completely or partially blocked by means of the second valve device, the process fluid can be directed across the membrane into the blood conducting section of the second filter device by simply switching the second valve device. In this way, it is advantageously easily and in a technically uncomplicated manner possible to obtain a reversion of the filtration direction common during a filtration, e.g., ultrafiltration, in which liquid is normally drawn from patient blood.

As both filter devices are designed or embodied as constituents of a single disposable, it may in certain exemplary embodiments advantageously be possible to do without a pre-switched or pre-arranged, respectively, sterile filter that is, for example, provided as a stationary filter and thus for re-use, and, therefore, to do without an integrity test associated therewith after a treatment.

As, according to the present invention, the performance of an integrity measurement (required for reusable filter device) of a filter device is advantageously not required anymore, a procedure of the medical blood treatment apparatus can advantageously be simplified. This can advantageously contribute to simplifying the technical and/or manual process steps which could be necessary prior to each treatment upon activating or preparing the extracorporeal blood circuit of a dialyzing machine. In this way, it can advantageously be possible to provide a substantially simplified system. This can advantageously contribute to increasing the system's safety.

As it is advantageously possible by means of the medical functional device according to the present invention, to replace two conventional filter devices provided for re-use or multiple use, respectively, by the medical functional device according to the present invention, it can advantageously be possible to save material and/or costs.

The one or more filter devices of the medical one-way functional device according to the present invention can in its/their size be adapted to the expected retention capacity for a treatment such that it is, due to this optimization, advantageously further possible to save costs. This primarily applies for the second filter device of the medical functional device.

Additionally, due to the filter devices herein provided as single-use filter devices, the medical functional device according to the present invention can advantageously contribute to reducing a contamination risk. In certain exemplary embodiments according to the present invention, this can moreover contribute to being able to keep sufficiently sterile conditions or quality criteria, respectively, of a sterilization for introducing an (optionally initially not sterile) process fluid into the extracorporeal blood circuit. In this way, it can, for example, advantageously be possible to avoid a contamination, in particular of the blood conducting lines.

In the following, the present invention is exemplarily described with respect to the appended drawings. In the figures of the drawings, identical reference numerals refer to same or identical elements.

DETAILED DESCRIPTION

Figure 1:
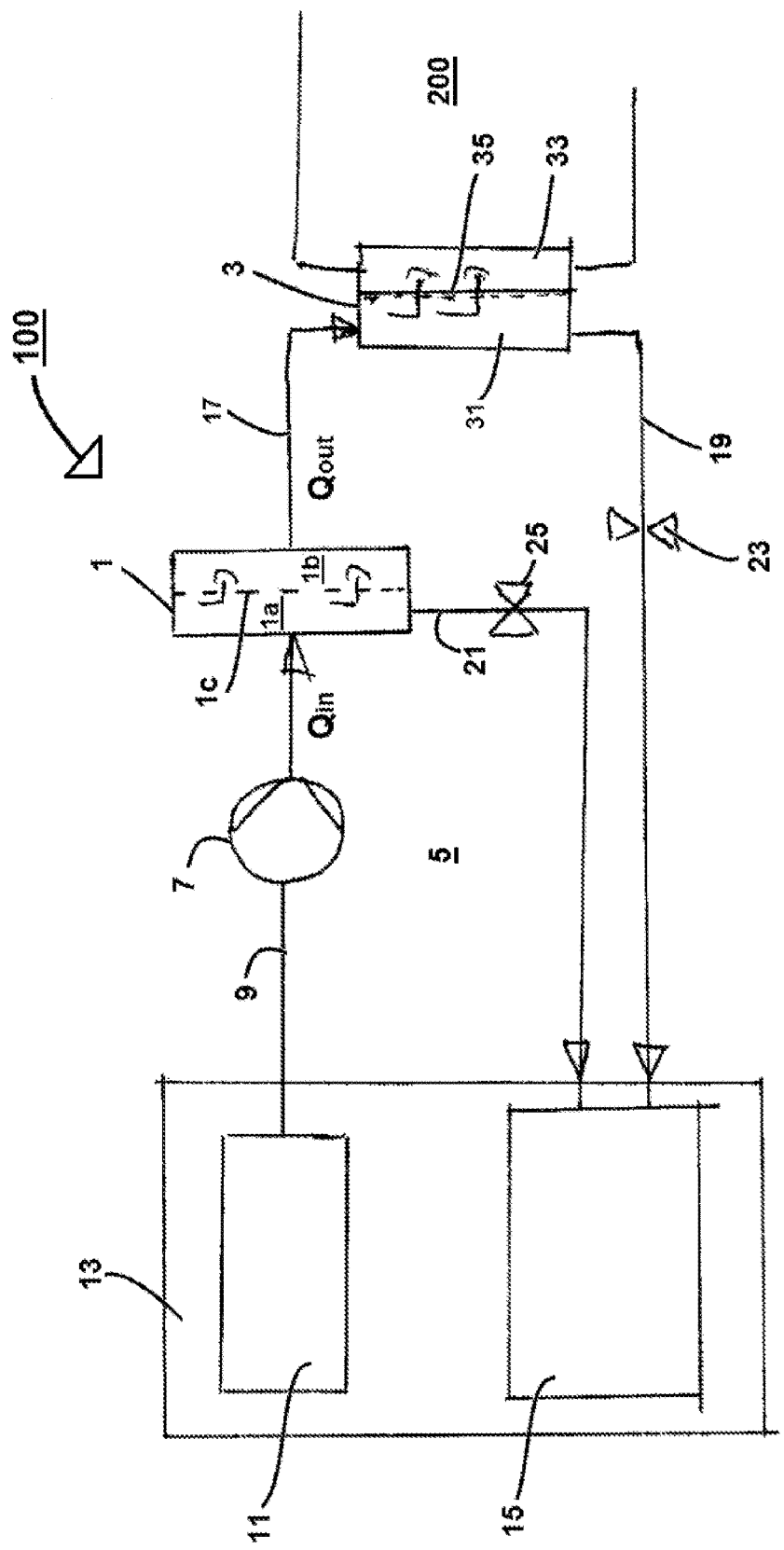
FIG. 1 shows a section of a medical functional device according to a first exemplary embodiment of the present invention in a schematically simplified manner.
Figure 2:
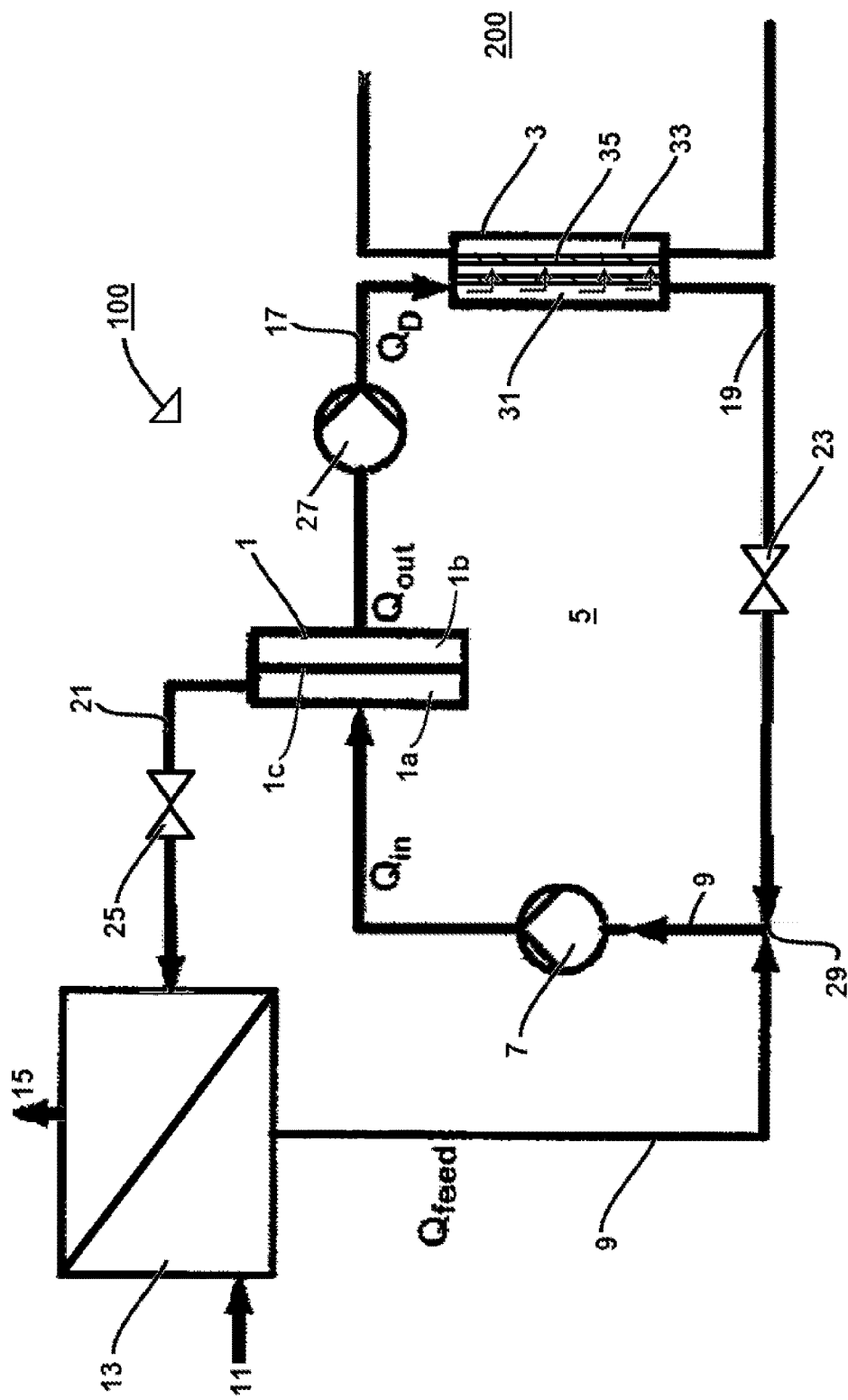
FIG. 2 shows a section of a medical functional device according to a second exemplary embodiment of the present invention in a schematically simplified manner.

In connection with certain exemplary embodiments according to the present invention, as they are also used in connection with FIGS. 1 and 2, the terms "upstream" and "downstream" each refer to the flow direction indicated by means of the arrows. The directions of the arrows respectively correspond to the flow direction; the arrows are each directed downstream.

FIG. 1 shows a section of a medical or medical-technical functional device 100 (in short: functional device) according to a first exemplary embodiment of the present invention.

The functional device 100 can be a disposable having two integrated filter stages and integrated process fluid and blood processing units.

As shown in FIG. 1, the medical functional device 100 comprises a first filter device 1 and a second filter device 3.

In some exemplary embodiments according to the present invention, the first filter device 1 is a sterile filter.

In certain exemplary embodiments according to the present invention—like the one shown in FIG. 1—the second filter device 3 is a blood filter.

The second filter device 3 is arranged in an extracorporeal blood circuit 200.

The first filter device 1 comprises a first section 1a as an inlet side for process fluid and a second section 1b as outlet side for process fluid.

The second filter device 3 comprises a process fluid conducting section 31 and a blood conducting section 33.

The sections 1a, 1b of the first filter device 1 and/or the sections 31, 33 of the second filter device 3 can each comprise two or more chambers. The chambers can be separated by means of hollow fiber capillary membranes 1c or 35, respectively.

The first filter device 1 and the second filter device 3 are part of a process fluid circuit 5.

The first filter device 1 and the second filter device 3 are disposables, i.e., they are discarded after their single use together with the medical functional device 100.

Both filter devices 1, 3 can be tested for integrity prior to their single use.

Advantageously, each filter device 1, 3 possesses a retention capacity sufficient for the intended purpose.

The functional device 100 comprises a first conveying device 7 for conveying process fluid.

In the exemplary embodiment shown in FIG. 1, the first conveying device 7 is arranged in a first line section 9 of the process fluid circuit 5 between a process fluid source 11 and the first filter device 1.

As shown here, the process fluid source 11 is part of a process fluid supply unit 13 which, in the specific exemplary embodiment of FIG. 1, comprises a reception device 15 for used process fluid in addition to the process fluid source 11.

In addition to the first line section 9 (between the process fluid source 11 and the first filter device 1), the process fluid circuit 5 comprises a second line section 17 (between the first filter device 1 and the second filter device 3), a third line section 19 which is arranged between the second filter device 3 and the reception device 15 for used process fluid, as well as a fourth line section 21 which is arranged between the first filter device 1 and the reception device 15 for used process fluid.

In some exemplary embodiments of the present invention, the process fluid circuit 5 or a part thereof forms a closed circuit or loop, respectively.

Not all elements, sections or constituents or parts, respectively, of the process fluid circuit 5 are in all exemplary embodiments really parts of the functional device 100. This can particularly apply for the third line section 19, preferably inclusive the conveying device 7, and the fourth line section 21.

In the third line section 19, a first valve device 23 is arranged downstream the second filter device 3. The first valve device 23 is provided to be controlled and/or switched such that a transfer of process fluid from the second filter device 3 to the reception device 15 for used process fluid via the third line section 19 of the process fluid circuit 5 is allowed or prevented.

In the fourth line section 21, a second valve device 25 is arranged downstream the first filter device 1. The second valve device 25 is provided to be controlled and/or switched such that a transfer of process fluid from the first filter device 1 to the reception device 15 for used process fluid via the fourth line section 21 of the process fluid circuit 5 is allowed or prevented.

During the use of the medical functional device 100 according to the present invention, for example, for rinsing and/or priming the extracorporeal blood circuit 200 or during an extracorporeal blood treatment, process fluid (Qin) is drawn from the process fluid source 11 and supplied to the first section 1a of the first filter device 1.

In the first filter device 1, the process fluid is regularly, preferably, completely filtrated across the hollow fiber membrane 1c into the second section 1b of the first filter device 1.

By means of the second valve device 25 which is not provided in certain exemplary embodiments according to the present invention or which is not used for the procedure described herein, a periodical cleaning of the hollow fiber membrane 1c can be performed in order to flush the hollow fiber membrane 1c in a case of cover layer formation. For this purpose, the second valve device 25 can be opened—at least temporarily—completely or partially.

The fourth line section 21 and the second valve device 25 of the exemplary embodiment shown in FIG. 1 are, however, not mandatorily required. In other exemplary embodiments of the medical functional device 100 according to the present invention, they can thus be omitted.

In certain exemplary embodiments, the second valve device 25 is embodied as a proportional valve.

Alternatively or additionally to the second valve device 25, an occluding pump is provided in some exemplary embodiments of the present invention.

In exemplary embodiments in which the second valve device 25 is designed as a proportional valve, a partial flow of the process fluid flowing through the first filter device 1 can be branched as a cross-flow and can be used for continuously reducing a cover layer formation on the membrane.

The process fluid (Qout) filtrated in the first filter device 1 is subsequently directed through the second line section 17 of the process fluid circuit 5 into the process fluid conducting section 31 of the second filter device 3.

In case of a blood treatment, for example, a dialysis treatment, the process fluid receives toxins from the blood in the second filter device 3 and is subsequently directed via the third line section 19 of the process fluid circuit 5 into the reception device 15 for used process fluid of the process fluid supply unit 13 (for example, the hydraulic system of a treatment apparatus, a balancing system, a charge-based system having one or two separated containers for the supply of fresh process fluid and the reception of used process fluid).

By completely or partially closing the third line section 19 by means of the first valve device 23—or alternatively an occluding pump—, the process fluid can be directed, i.e., filtrated, across the hollow fiber membrane 35 into the blood conducting section 33 of the second filter device 3.

By appropriately switching the first valve device 23, switching between treatment, priming, blood return, bolus addition, etc., can be obtained in an advantageously simple and technically uncomplicated manner.

FIG. 2 shows a section of a medical functional device 100 according to an alternative second exemplary embodiment of the present invention.

The first filter device 1 and/or the second filter device 3 are designed analogously to the first exemplary embodiment of the medical functional device 100 according to the present invention described in FIG. 1.

In addition to the first conveying device 7, a second conveying device 27 is arranged in the exemplary embodiment shown in FIG. 2. It is arranged in the second line section 17 of the process fluid circuit 5 between the first filter device 1 and the second filter device 3—downstream the first filter device 1.

In other exemplary embodiments, the second conveying device 27 can also be arranged at another position than between the first filter device 1 and the second filter device 3. For example, the second conveying device 27 can be arranged in flow direction of the process fluid upstream the first filter device 1.

The process fluid circuit 5 comprises a branching 29 at which the third line section 19 is brought in fluid communication with the first line section 9.

At the branching 29, used process fluid flowing out of the second filter device 3 through the third line section 19 is combined with fresh process fluid (Qfeed) flowing out of the process fluid source 11 through the first line section 9.

During an extracorporeal blood treatment method, process fluid is flowing from the process fluid source 11 as a flow Qfeed—propelled by means of the first conveying device 7—into the first filter device 1. A part thereof leaves the first conveying device 1 as a flow Qout. After passing the second conveying device 27, the process fluid is introduced as a flow QD via the second line section 17 into the second filter device 3.

In the second filter device 3, the process fluid, e.g., dialyzing liquid, is, for example, during a hemodialysis directed along the blood also flowing according to the counter flow principle. After exiting the second filter device 3, the process fluid reaches the third line section 19 where it is in turn directed to the first filter device 1 behind the branching 29 as a flow Qin. From the first filter device 1, the process fluid can be returned back to the reception device 15 for used process fluid via the fourth line section 21. Alternatively, it can be discarded.

In some exemplary embodiments it is intended to remove used process fluid from the process fluid circuit 5 via a corresponding drain line (not shown in FIG. 2) and/or a balancing unit (not shown in FIG. 2). The amount of process fluid removed from the process fluid circuit 5 can be compensated by adding fresh process fluid from the process fluid source 11 via the first line section 9.

For performing an extracorporeal blood treatment process, operating the first conveying device 7 for conveying the process fluid through the process fluid circuit 5 ensures a sufficient conveyance. The second conveying device 27 has thus not necessarily to be operated during the blood treatment process.

For priming or filling the extracorporeal blood circuit 200, process fluid, for example, dialyzing liquid, is conveyed from the process fluid source 11, e.g., an online dialyzing liquid source, to the first filter device 1.

In this first step of a cascade filtration, in the example of FIG. 2, the process fluid is filtered by means of a sterile filter module of the first filter device 1. The process fluid passes through the hollow fiber membrane 35 of the first filter device 1 and is thereby cleaned, in particularly sterile-filtered.

When the second valve device 25 is closed, a so called "dead end" filtration occurs at the first filter device 1. As the flow path via the first section's 1a outlet of the first filter device into the fourth line section 21 is blocked, the process fluid has to pass the hollow fiber membrane 1c.

After having left the first filter device 1 with a first flow Qout, the process fluid passes the conveying device 27 and reaches the second filter device 3 as a flow QD.

By means of a pressure difference between a process fluid conducting section 31 and the hollow fiber membrane lumen, the process fluid can—in this second step of the cascade filtration—enter the lumen of the blood conducting section 33 of the second filter device 3 across hollow fiber membrane 35 in the second filter device 3.

The pressure difference can be a trans-membrane pressure drop. Blocking the through-flow of the process fluid through the third line section 19 by means of the first valve device 23 can favor the transfer of the process fluid into the extracorporeal blood circuit 200.

In the extracorporeal blood circuit 200, the process fluid can be used for rinsing corresponding blood conducting lines and/or devices.

Moreover, blocking the second valve device 25 can prevent process fluid draining out of the first filter device 1 to the process fluid source 11.

The external medical functional device according to the present invention can advantageously substantially or exclusively change between a rinsing or priming and/or filling process and blood treatment process only by correspondingly switching the first and the second valve devices 23, 25 and/or by actuating the first conveying device 7.

The invention claimed is:

1. A disposable blood cassette for extracorporeally treating blood of a patient, the disposable blood cassette comprising:
    at least a portion of a process fluid circuit configured to be connected to a process fluid source to receive a process fluid from the process fluid source;
    a first filter device arranged within the portion of the process fluid circuit;
    a second filter device arranged within the portion of the process fluid circuit;
    a first conveying device arranged in the portion of the process fluid circuit between the first filter device and the second filter device and upstream of the first filter device, the first conveying device operable to convey the process fluid from the process fluid source through the first conveying device and then to the first filter when the disposable blood cassette is connected to the process fluid source and operably coupled to a medical blood treatment apparatus;
    a first valve device arranged in the portion of the process fluid circuit between the first conveying device and the second filter device and downstream of the second filter device;
    a branch arranged within the portion of the process fluid circuit between the first conveying device and the first valve device and downstream of the first valve device, the branch configured to be connected to the process fluid source to mix the process fluid from the process fluid source with all of the process fluid from the second filter device upstream of the first conveying device, such that the first conveying device is configured to convey all of the process fluid from the second filter device to the first filter device via the branch and the first valve device; and
    at least a portion of an extracorporeal blood circuit, wherein the disposable blood cassette is configured to be controlled upon coupling or connecting the disposable blood cassette with the medical blood treatment apparatus, and the first valve device and the first conveying device are operable in a manner to introduce the process fluid into at least one of the portion of the process fluid circuit and the portion of the extracorporeal blood circuit.

2. The disposable blood cassette according to claim 1, further comprising a second conveying device arranged in the portion of the process fluid circuit between the first filter device and the second filter device and downstream of the first filter device and configured to convey the process fluid within the portion of the process fluid circuit.

3. The disposable blood cassette according to claim 1, wherein the portion of the process fluid circuit is configured to receive the process fluid from the process fluid source at the branch upstream of the first conveying device.

4. The disposable blood cassette according to claim 1, wherein the first conveying device is a pump configured for proportional regulation and is arranged downstream of the second filter device in the portion of the process fluid circuit.

5. The disposable blood cassette according to claim 1, wherein the second filter device is a blood filter device of the portion of the extracorporeal blood circuit.

6. The disposable blood cassette according to claim 1, wherein at least one of the first conveying device and the first valve device is configured to be actuated by one or more actuators of the medical blood treatment apparatus upon coupling or connecting the disposable blood cassette with the medical blood treatment apparatus in order to rinse or fill the portion of the extracorporeal blood circuit or for blood return or bolus addition.

7. The disposable blood cassette according to claim 1, wherein at least one of the first conveying device and the first valve device is configured to be controlled by one or more actuators of the medical blood treatment apparatus upon coupling or connecting the disposable blood cassette with the medical blood treatment apparatus such that the disposable blood cassette is switchable between a rinsing or filling process and an extracorporeal blood treatment process.

8. The disposable blood cassette according to claim 1, wherein the first conveying device is configured to be actuated by an actuator of the medical blood treatment apparatus upon coupling or connecting the disposable blood cassette with the medical blood treatment apparatus.

9. The disposable blood cassette according to claim 1, wherein the first conveying device is selected from the group consisting of a membrane pump, a peristaltic pump and an impeller pump.

10. The disposable blood cassette according to claim 1, wherein at least one of the first filter device and the second filter device comprise hollow fiber modules having hollow fiber capillary membranes.

11. The disposable blood cassette according to claim 1, comprising a process fluid return line, wherein the first filter is in fluid communication with the process fluid return line, and wherein a second valve device or a second occluding pump is arranged downstream of the first filter device in the process fluid return line.

12. A medical treatment apparatus comprising:
a disposable blood cassette comprising:
at least a portion of a process fluid circuit configured to be connected to a process fluid source to receive a process fluid from the process fluid source,
a first filter device arranged within the portion of the process fluid circuit,
a second filter device arranged within the portion of the process fluid circuit,
a first conveying device arranged in the portion of the process fluid circuit between the first filter device and the second filter device and upstream of the first filter device, the first conveying device operable to convey the process fluid from the process fluid source through the first conveying device and then to the first filter when the disposable blood cassette is connected to the process fluid source and operably coupled to a medical blood treatment apparatus,
a first valve device arranged in the portion of the process fluid circuit between the first conveying device and the second filter device and downstream of the second filter device,
a branch arranged within the portion of the process fluid circuit between the first conveying device and the first valve device and downstream of the first valve device, the branch configured to be connected to the process fluid source to mix the process fluid from the process fluid source with all of the process fluid from the second filter device upstream of the first conveying device, such that the first conveying device is configured to convey all of the process fluid from the second fluid device to the first device via the branch and the first valve device, and
at least a portion of an extracorporeal blood circuit, wherein the disposable blood cassette is configured to be controlled upon coupling or connecting the disposable blood cassette with the medical blood treatment apparatus, and the first valve device and the first conveying device are operable in a manner to introduce the process fluid into at least one of the portion of the process fluid circuit and the portion of the extracorporeal blood circuit; and
a process fluid supply unit comprising:
the process fluid source, and
a reception device configured to receive used process fluid from the disposable blood cassette.

13. The disposable blood cassette according to claim 2, wherein at least one of the first and second conveying devices is configured to be actuated by at least one actuator of the medical blood treatment apparatus upon coupling or connecting the disposable blood cassette with the medical blood treatment apparatus.

14. The disposable blood cassette according to claim 2, wherein at least one of the first and second conveying devices is selected from the group consisting of a membrane pump, a peristaltic pump and an impeller pump.

15. The medical treatment apparatus according to claim 12, wherein a second blocking device, a second valve device, or a second occluding pump device is arranged in the portion of the process fluid circuit between the first filter device and the reception device.

16. The disposable blood cassette according to claim 1, wherein the second filter device is arranged within the portion of the process fluid circuit and within the portion of the extracorporeal blood circuit.

* * * * *